US009492321B2

(12) United States Patent
Gunn et al.

(10) Patent No.: US 9,492,321 B2
(45) Date of Patent: Nov. 15, 2016

(54) BUBBLE-FREE MICROFLUIDIC VALVE SYSTEMS AND METHODS

(71) Applicant: NOVARTIS AG, Basel (CH)

(72) Inventors: Nicholas Max Gunn, Newport Beach, CA (US); Andrew David Johnson, Tustin, CA (US)

(73) Assignee: Novartis AG, Basel (CH)

( * ) Notice: Subject to any disclaimer, the term of this patent is extended or adjusted under 35 U.S.C. 154(b) by 67 days.

(21) Appl. No.: 14/618,102

(22) Filed: Feb. 10, 2015

(65) Prior Publication Data
US 2015/0150720 A1 Jun. 4, 2015

Related U.S. Application Data

(62) Division of application No. 13/975,320, filed on Aug. 24, 2013, now abandoned.

(51) Int. Cl.
*A61F 9/007* (2006.01)
*F16K 99/00* (2006.01)
*A61F 9/00* (2006.01)

(52) U.S. Cl.
CPC ....... *A61F 9/00781* (2013.01); *F16K 99/0015* (2013.01); *F16K 99/0057* (2013.01); *A61F 9/0017* (2013.01); *A61M 2205/0244* (2013.01); *A61M 2210/0612* (2013.01); *B81B 2201/054* (2013.01); *B81B 2203/0127* (2013.01); *F16K 2099/0088* (2013.01); *Y10T 137/7895* (2015.04)

(58) Field of Classification Search
CPC ............. A61F 9/00781; A61F 9/0017; F16K 2099/0084; F16K 99/0015; F16K 99/0001; F16K 99/0034; F16K 99/0055; F16K 99/0057; F16K 99/0059; F16K 2099/0088; F16K 2099/0082; A61M 2210/0612; A61M 2205/0244; A61M 5/16881; Y10T 137/7891; Y10T 137/7895; B81B 2201/054; B81B 2203/0127
See application file for complete search history.

(56) References Cited

U.S. PATENT DOCUMENTS

| 4,241,756 | A | * | 12/1980 | Bennett | A61M 16/20 137/496 |
|---|---|---|---|---|---|
| 6,056,269 | A | | 5/2000 | Johnson et al. | |
| 6,579,235 | B1 | | 6/2003 | Abita et al. | |
| 7,544,176 | B2 | | 6/2009 | Rodgers et al. | |

(Continued)

OTHER PUBLICATIONS

International Searching Authority, International Preliminary Report on Patentability, PCT/US2014/039582, Feb. 23, 2016, 5 pages.

(Continued)

*Primary Examiner* — Adam Marcetich
(74) *Attorney, Agent, or Firm* — Kenneth D. Bassinger

(57) ABSTRACT

A microfluidic valve for implantation in an eye of a patient is disclosed. The valve may include a chamber formed between a substrate and a flexible membrane. The valve may also include a boss disposed in the chamber and having a top edge in selective contact with the flexible membrane. The top edge includes a relief portion and a non-relief portion, with the relief portion being structurally arranged so that a pressure required to separate the membrane from the relief portion is less than a pressure required to separate the membrane from the non-relief portion. The valve also may include an inlet extending through the boss and the substrate through which fluid enters the chamber and an outlet configured to allow fluid to exit the chamber. Methods for priming a microfluidic valve are also disclosed.

13 Claims, 7 Drawing Sheets

(56) References Cited

U.S. PATENT DOCUMENTS

| | | | |
|---|---|---|---|
| 2002/0013545 A1 | 1/2002 | Soltanpour et al. | |
| 2002/0087111 A1 | 7/2002 | Ethier et al. | |
| 2002/0156413 A1 | 10/2002 | Williams et al. | |
| 2002/0165478 A1 | 11/2002 | Gharib et al. | |
| 2002/0169468 A1 | 11/2002 | Brown | |
| 2003/0002995 A1* | 1/2003 | Urano | F04B 43/046 417/322 |
| 2003/0146401 A1* | 8/2003 | Wetzel | F15C 5/00 251/61.1 |
| 2003/0234376 A1 | 12/2003 | Cabuz et al. | |
| 2004/0073156 A1 | 4/2004 | Brown | |
| 2004/0228734 A1 | 11/2004 | Jeon et al. | |
| 2005/0067029 A1 | 3/2005 | Henning et al. | |
| 2005/0273033 A1 | 12/2005 | Grahn et al. | |
| 2006/0000459 A1* | 1/2006 | Freeman | F01M 13/0011 123/574 |
| 2007/0243111 A1 | 10/2007 | Momose | |
| 2007/0251592 A1* | 11/2007 | Christenson | F15C 5/00 137/859 |
| 2008/0066810 A1* | 3/2008 | Barak | A61M 39/22 137/493.8 |
| 2008/0082077 A1* | 4/2008 | Williams | A61M 1/0058 604/506 |
| 2009/0196903 A1 | 8/2009 | Kliman | |
| 2010/0042209 A1 | 2/2010 | Guarnieri | |
| 2010/0122733 A1* | 5/2010 | Grygus | F16K 99/0001 137/14 |
| 2010/0249691 A1 | 9/2010 | Van Der Mooren et al. | |
| 2011/0071454 A1 | 3/2011 | Dos Santos et al. | |
| 2011/0082385 A1 | 4/2011 | Diaz et al. | |
| 2011/0144617 A1 | 6/2011 | Meng et al. | |
| 2011/0203700 A1 | 8/2011 | Scholten et al. | |
| 2011/0282328 A1 | 11/2011 | Ambati et al. | |
| 2012/0039770 A1 | 2/2012 | Namkoong et al. | |
| 2012/0302861 A1 | 11/2012 | Marshall et al. | |
| 2012/0316492 A1 | 12/2012 | Chappel | |
| 2013/0000765 A1 | 1/2013 | Fernandes et al. | |
| 2013/0150774 A1 | 6/2013 | Field et al. | |
| 2013/0150775 A1 | 6/2013 | Dos Santos et al. | |
| 2013/0150777 A1 | 6/2013 | Boehm et al. | |
| 2013/0150779 A1* | 6/2013 | Field | A61F 9/00781 604/9 |
| 2013/0211312 A1 | 8/2013 | Gelvin | |
| 2013/0317413 A1 | 11/2013 | Field et al. | |

OTHER PUBLICATIONS

International Searching Authority, International Search Report, PCT/US2014/039582, Oct. 22, 2014, 3 pages.

International Searching Authority, Written Opinion, PCT/US2014/039582, Oct. 22, 2014, 4 pages.

* cited by examiner

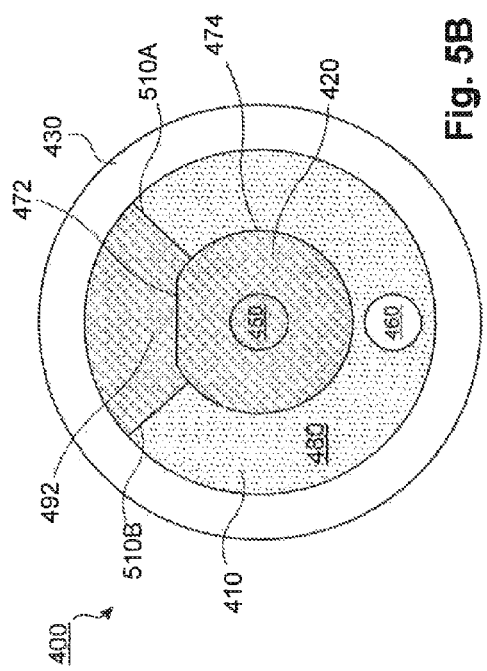
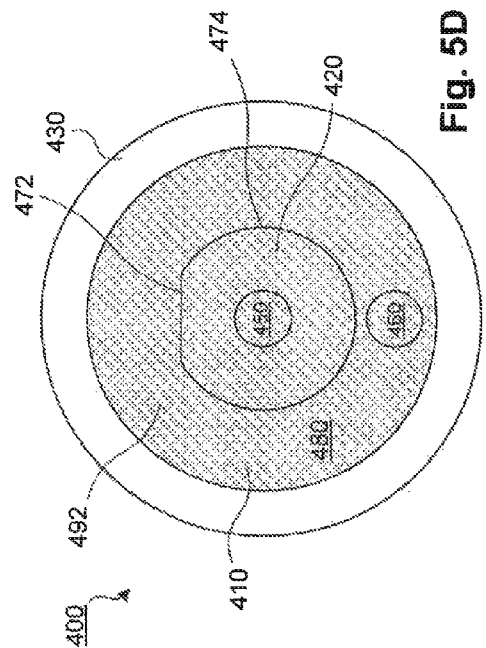
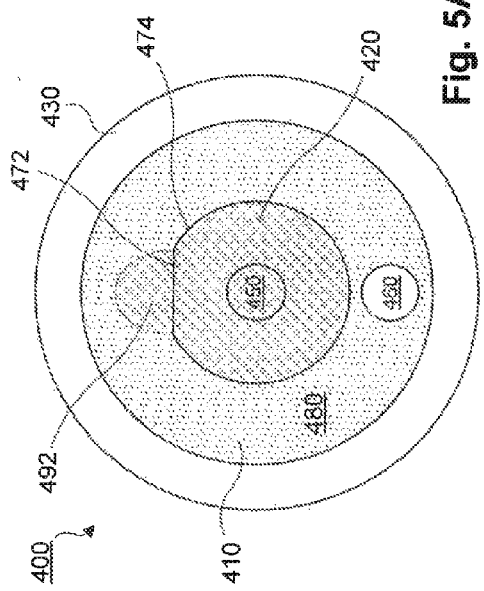
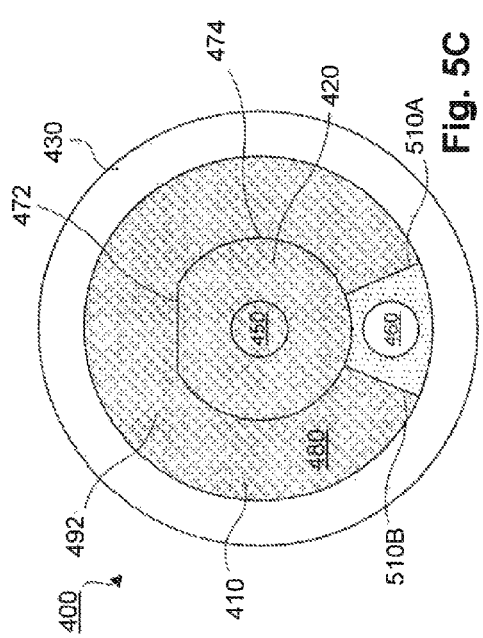

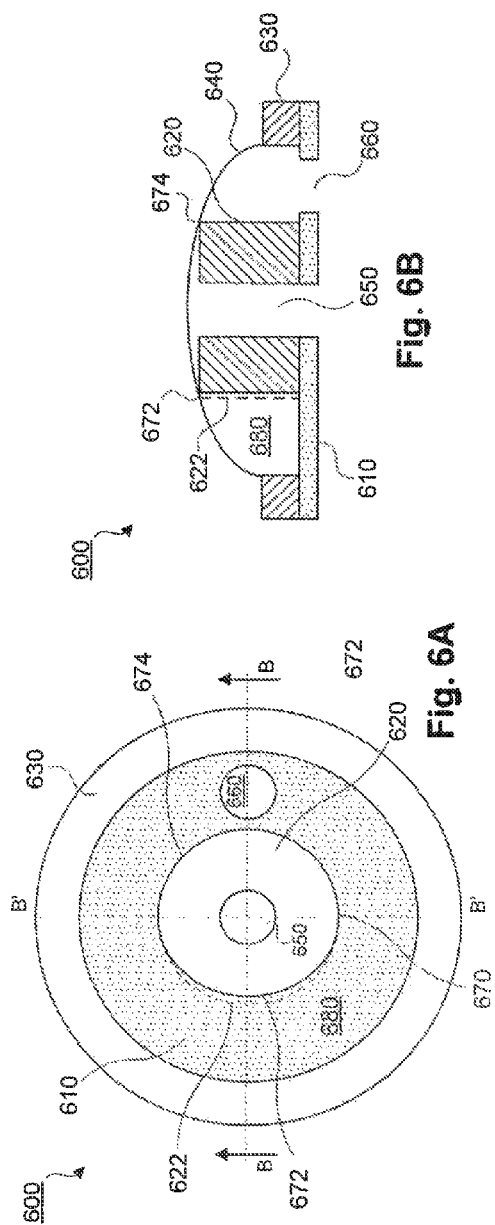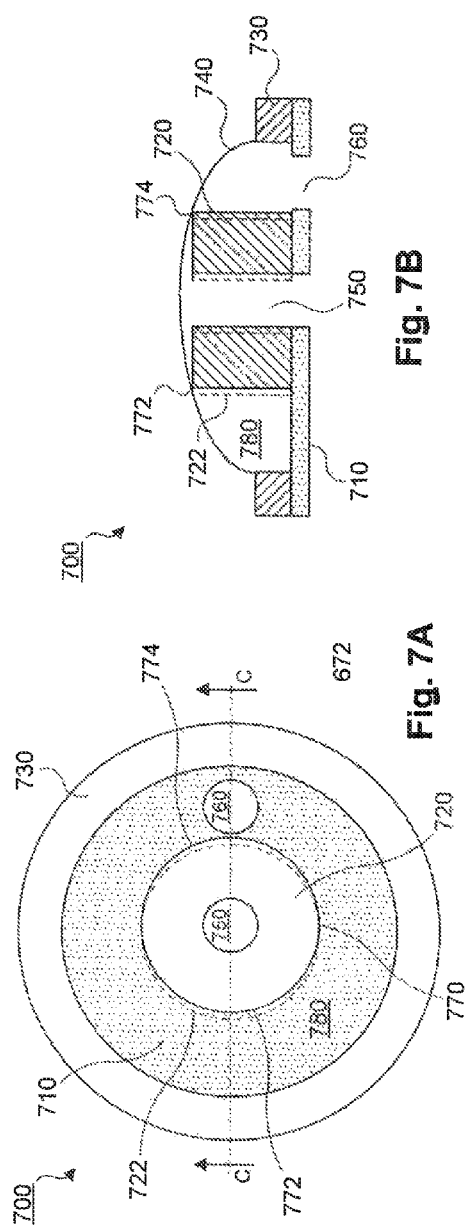

BUBBLE-FREE MICROFLUIDIC VALVE SYSTEMS AND METHODS

CROSS-REFERENCE TO RELATED APPLICATION

This application is a divisional of U.S. application Ser. No. 13/975,320 filed Aug. 24, 2013.

BACKGROUND

The present disclosure relates generally to microfluidic valve systems and methods for ophthalmic treatments. More particularly, the present disclosure relates to microfluidic valve systems that may be purged of air or other gas and methods for purging the air or other gas from the microfluidic valve systems.

Glaucoma, a group of eye diseases affecting the retina and optic nerve, is one of the leading causes of blindness worldwide. Most forms of glaucoma result when the intraocular pressure (TOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye 100 that helps to explain the processes of glaucoma. In FIG. 1, representations of the lens 110, cornea 120, iris 130, ciliary body 140, trabecular meshwork 150, Schlemm's canal 160, and the edges of the sclera 170 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber 180. The edge of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The sclera 170, the white of the eye, connects to the cornea 120, forming the outer, structural layer of the eye. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

As part of a method for treating glaucoma, a doctor may implant a device in a patient's eye. The device may monitor the pressure in a patient's eye and facilitate control of that pressure by allowing excess aqueous humor to flow from the anterior chamber of the eye to a drainage site, relieving pressure in the eye and thus lowering IOP. Valves within the device may permit and prevent the flow of fluids such as the aqueous humor. An accurate indication of the pressure about the patient's eye may be made in order to determine when the aqueous humor should be drained and when it should be maintained. In order to accurately respond to the pressure, the valves should be primed so as to decrease the formation of anomalies therein. However, the priming of valves of the size required for implantation into a patient's eye has not been entirely satisfactory.

The system and methods disclosed herein overcome one or more of the deficiencies of the prior art.

SUMMARY

In one exemplary aspect, the present disclosure is directed to a microfluidic valve for implantation in an eye of a patient. The valve includes a chamber formed between a substrate and a flexible membrane and a boss disposed in the chamber with a top edge in selective contact with the flexible membrane. The top edge includes a relief portion and a non-relief portion. The relief portion is structurally arranged so that a pressure required to separate the membrane from the relief portion is less than a pressure require to separate the membrane from the non-relief portion. The valve further includes an inlet extending through the boss and the substrate through which fluid may enter the chamber and an outlet configured to allow fluid to exit the chamber.

In an additional exemplary aspect, the present disclosure is directed to another microfluidic valve for implantation in an eye of a patient. The valve includes a chamber that has a boundary surface comprising a first wall and a second wall. The second wall opposes, or is opposite, the first wall. The valve also includes a valve portion configured to regulate fluid flow into the chamber. Additionally, the valve includes an inlet that is configured to allow a fluid to flow through the valve portion and into the chamber and an outlet configured to allow the fluid to flow out of the chamber at a location accessible by fluid flowing to the outlet from more than one direction. The outlet is bounded by a first priming block disposed between the outlet and the first wall and by a second priming block disposed between the outlet and the second wall.

In yet another exemplary aspect, the present disclosure is directed to a method of priming a valve in an intraocular device. The method includes steps of introducing a pressurized fluid to a valve and of breaking a seal of the valve by displacing a membrane relative to a relief portion of a boss structure so that the pressurized fluid flows into a chamber at the relief portion. The pressurized fluid is restricted from flowing into the chamber along a non-relief portion of the boss structure. The method further includes a step of directing the pressurized fluid to a valve outlet such that the chamber is filled with the pressurized fluid.

In another exemplary aspect, the present disclosure is directed to a method of priming a valve in an intraocular device. The method includes steps of introducing a pressurized fluid to a valve and of breaking a seal of the valve by displacing a membrane relative to a relief portion of a boss structure so that pressurized fluid flows into a chamber and toward a valve outlet in a first flow direction through a first portion of the chamber and toward the valve outlet in a second flow direction through a second portion of the chamber. The method further includes a step of preventing a front of the fluid flowing in the first flow direction from passing into the second portion of the chamber.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure

FIGS. 5A, 5B, 5C, and 5D are top views showing the microfluidic chamber of FIG. 4A-D in various stages of priming.

FIG. 6A is a top view of another valve such as may be used in the intraocular implant according to exemplary aspects of the present disclosure.

FIG. 6B is a cross-sectional view of the valve of FIG. 6A according to exemplary aspects of the present disclosure.

FIG. 7A is a top view of an additional valve such as may be used in the intraocular implant according to exemplary aspects of the present disclosure.

FIG. 7B is a cross-sectional view of the valve of FIG. 7A according to exemplary aspects of the present disclosure.

DETAILED DESCRIPTION

Figure 1:
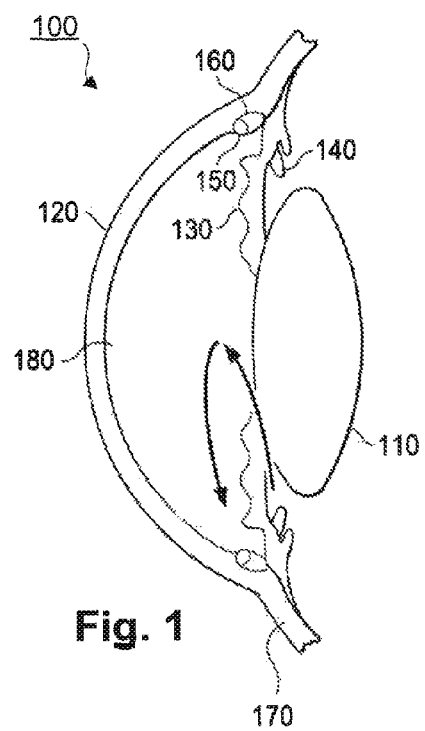
FIG. 1 is a cross-sectional view of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to systems and methods for ensuring air or other gas is fully purged from a valve in an intraocular device, by guiding the liquid from a valve inlet to a valve outlet. Air or other gas within such a valve may degrade performance of the implanted intraocular device. In some aspects described herein, the valve includes a flexible membrane that seals against a structure, such as a boss. When purging the air or other gas, a saline solution is flushed through the valve. The valve arrangement controls the flow location of the solution, reducing the likelihood of bubbles becoming trapped within the valve. The systems and methods disclosed herein may thereby enable valves to more accurately respond to pressures, such as that exerted by aqueous humor in an intraocular device, potentially providing more effective treatment and greater customer satisfaction. In some aspects, the intraocular device is an intraocular pressure (TOP) controlling device, such as a glaucoma drainage device (GDD) that alleviates elevated IOP in a patient's eye.

Figure 2:
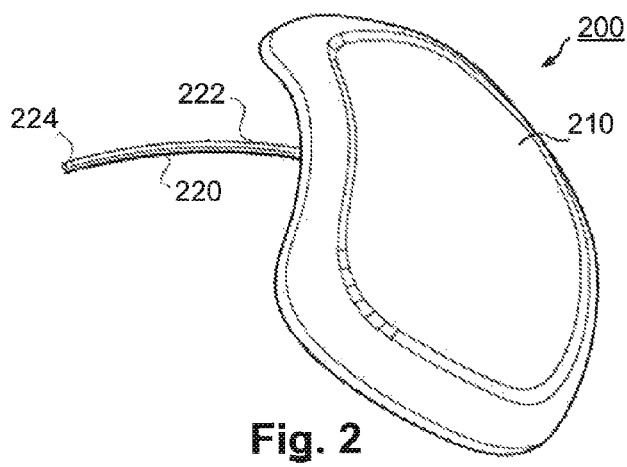
FIG. 2 is a perspective view of an intraocular implant that carries a microfluidic chamber.

FIG. 2 is a schematic diagram of an intraocular implant or device 200 useable in the monitoring and treatment of a patient's eye. As depicted, the intraocular device 200 is a GDD. The intraocular device 200 includes a body referred to herein as a plate 210 with a drainage tube 220 that extends from the plate 210. The drainage tube 220 includes a proximal end portion 222 that couples the tube to one or more structures internal to the plate 210. A distal end portion 224 of the drainage tube 220 may be coupled to the eye of a patient to allow for the monitoring of pressure and/or the drainage of fluid. Embodiments of the intraocular device 200 may include additional tubes for priming and/or for the detection of pressure at other location. The drainage tube 220 forms part of a passive valve system. An associated valve will be discussed in greater detail below.

Figure 3:
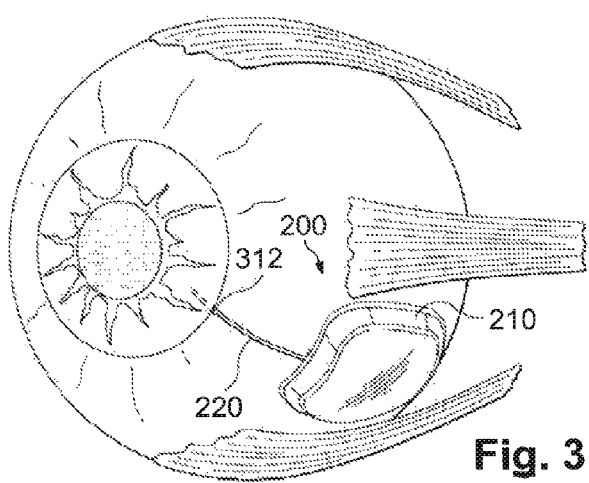
FIG. 3 is a perspective view of an intraocular implant as situated proximate an eye according to an exemplary aspect of the present disclosure.

FIG. 3 is a schematic diagram of an eye of a patient whose IOP is being monitored and/or who is receiving treatment with the intraocular device 200. The intraocular device 200 may be a GDD as depicted in FIG. 2. The plate 210 may include or be arranged to carry various components of an IOP control system, including for example, one or more of a power source, a processor, a memory, a data transmission module, and a flow control mechanism (e.g., a valve system). It may also carry one or more pressure sensor systems.

The plate 210 is configured to fit at least partially within the subconjunctival space and is sized within a range between about 15 mm×12 mm to about 30 mm×15 mm and has a thickness less than about 2 mm thick, preferably less than about 1 mm thick. The plate 210 may be formed to the radius of the eye globe (about 0.5 inches). It may be rigid and preformed with a curvature suitable to substantially conform to the globe or it may be flexible and can flex to conform to the globe. Some embodiments are small enough that conforming to the globe provides little benefit in comfort or implantation technique. The above dimensions are exemplary only, and other sizes and arrangements are contemplated herein.

In some embodiments, the drainage tube 220 extends from an anterior side of the plate 210 and is sized and arranged to extend into the anterior chamber 180 (as seen in FIG. 1) of the eye through a surgically formed opening 312 in the sclera. The drainage tube 220 may be used to measure pressure in addition to facilitating drainage. The drainage tube 220 includes a first open end that may be disposed at a location where pressure measurements may be desired (in this instance within the anterior chamber 180), and at least one lumen that extends to a second open end that may be disposed within or connected to the plate 210.

Prior to placement around a patient's eye as depicted in FIG. 3, a chamber within the plate 210 may be primed by the injection of liquid that displaces a gas from the valve and/or other chambers within the device 200. The liquid may be injected through the tube 220 until some liquid may exit through a valve outlet. Thus in some embodiments, one or more valves within plate 210 may be primed prior to positioning beside a patient's eye and being put in communication with the anterior chamber of the eye as depicted in FIG. 3.

Figure 4A:
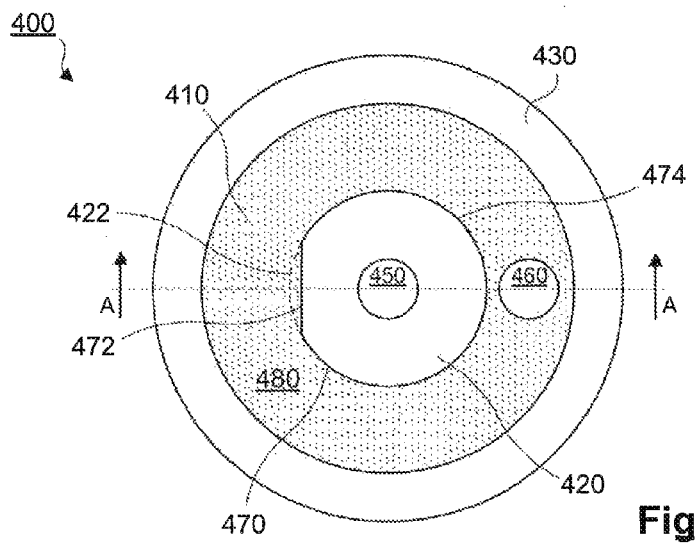
FIG. 4A is a top view of a valve such as may be used in the intraocular implant according to exemplary aspects of the present disclosure.

FIG. 4A is a top view of a portion of a valve 400 such as may be present in the intraocular device 200 of FIGS. 2 and 3. The valve 400 includes a substrate 410 upon which a number of additional features may be present. As depicted, the valve 400 further includes a boss 420 and a membrane retainer 430 on the surface of the substrate 410. In some embodiments, the substrate 410, the boss 420, and the membrane retainer 430 are made from a single piece of material. In other embodiments, these components may be fabricated separately and joined together afterwards. The boss 420 may be a generally cylindrical structure extending out from the substrate 410 until it contacts a membrane 440. In FIG. 4A, the membrane 440 is not clearly shown. However, the membrane 440 is more clearly seen in FIG. 4B. The valve 400 further includes the valve inlet 450 and a valve outlet 460.

As depicted in FIG. 4A, the boss 420 but does not have an entirely circular cross-section as viewed from above. As mentioned, the boss 420 extends up from the substrate 410 until it contacts the membrane 440, which may have a dome shape. The boss 420 and the membrane 440 contact at a sealing interface or top edge 470 of the boss 420. At least the top edge 470 of the boss 420 includes a relief portion 472 and a non-relief portion 474. As depicted in FIG. 4A, the relief portion 472 may be substantially straight or flattened, while the non-relief portion 474 is a circular edge portion. A dashed curve 422 in FIG. 4A depicts the boss 420 as it would appear if the relief portion 472 were not present. The straightened relief portion 472 may be an edge that is orthogonal to an imaginary axis connecting the valve inlet 450 to the valve outlet 460. In some embodiments, the bottom edge of the boss 420 may not have the same shape as the top edge 470. The volume defined between the membrane retainer 430 and the boss 420 is a chamber 480 of the valve 400. As depicted, the chamber 480 has a toroidal shape, though other shaped chambers may be used in other embodiments.

Figure 4B:
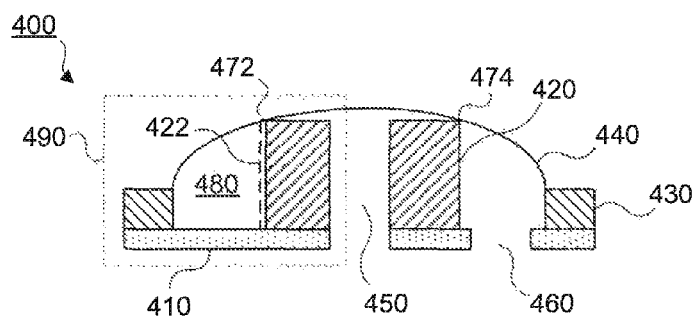
FIG. 4B is a cross-sectional view of the valve of FIG. 4A according to exemplary aspects of the present disclosure.

FIG. 4B is a cross-sectional view of the valve 400 depicted in FIG. 4A. The cross-sectional view of FIG. 4B is along the line A-A as depicted in FIG. 4A. FIG. 4B may more clearly depict aspects of the membrane 440 and its contact at two points along the top edge 420. FIG. 4B also depicts the attachment of the edges of the membrane 440 to the membrane retainer 430. The membrane 440 may be attached to the membrane retainer 430 in many different ways, including deposition of the membrane 440 across the top of the membrane retainer 430, bonding the membrane 440 to the membrane retainer 430, mechanically pinching the membrane 440 within the membrane 430, and other means.

The two depicted contact points include a point on the relief portion 472 and a point on the non-relief portion 474. In FIG. 4A, the valve inlet 450 and the boss 420 are centered underneath the membrane 440. The flexible membrane 440 may exert a pressure all along the top edge 470, including both the relief portion 472 and the non-relief portion 474. Because the relief portion 472 is closer to the center of the valve 400, when the membrane 440 begins to lift off the boss 420, fluid flows first at the location of the relief portion 472, because the change in the height of the membrane 440 allows clearance at relief 472 first. The relief portion 472 is arranged so that the portion of the membrane 440 adjacent the relief portion 472 deflects at a lower pressure than the portion of the membrane 440 adjacent the non-relief portion 474. The chamber 480 is bounded on the sides by the membrane retainer 430 and the boss 420, and on the top and bottom by the membrane 440 and the substrate 410, respectively.

Figure 4C:
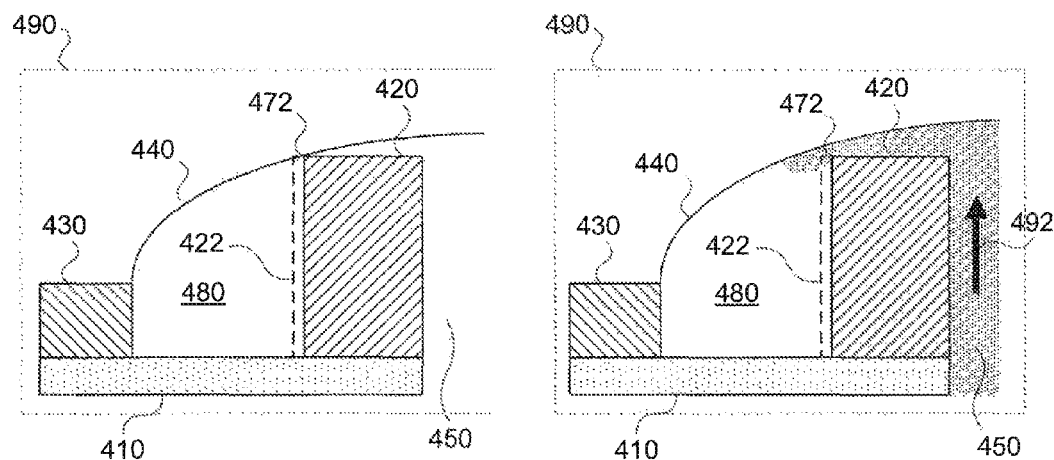
FIG. 4C is a cross-sectional view showing a portion of the valve of FIG. 4B in a closed state according to exemplary aspects of the present disclosure.

FIG. 4C presents an additional, enlarged view of a region of interest 490 seen in the FIG. 4B. This region of interest 490 includes portions of the substrate 410, the boss 420, the membrane retainer 430, the membrane 440, and the chamber 480. As depicted in FIG. 4C, the valve 400 is in a closed state: there is no separation between the membrane 440 and the relief portion 472 of the boss 420.

Figure 4D:
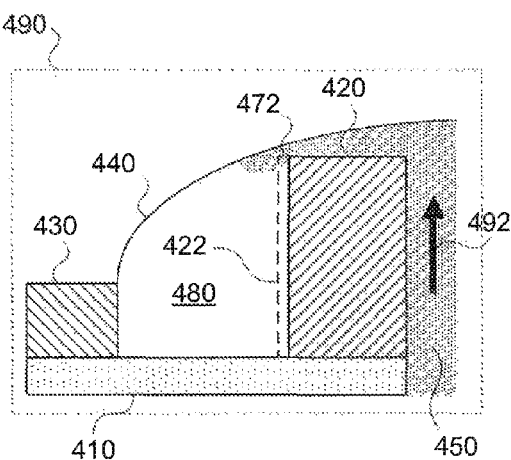
FIG. 4D is a cross-sectional view showing the portion of the valve of FIG. 4B in an open state according to exemplary aspects of the present disclosure.

FIG. 4D presents an additional, enlarged view of the region of interest 490 as seen in FIG. 4B. FIG. 4D is similar in many ways to FIG. 4C. However, as depicted in FIG. 4D, the valve 400 is in an open state caused by a pressurized liquid 492, which is flowing up through the inlet 450. For example, the valve inlet 450 may be coupled to a liquid source such as the anterior chamber 180 (FIG. 1) of an eye that has an elevated IOP. The pressure within the anterior chamber 180 pressurizes the liquid which may be routed from the anterior chamber, through a tube such as tube 220 of FIGS. 2 and 3, and into the valve inlet 450. Alternatively, the liquid 492 may be a saline solution injected by a doctor or technician during a priming process prior to implantation.

When the upward pressure exerted by the liquid 492 on the boss 420 and the membrane 440 is greater than a downward pressure exerted by the membrane 440 on the top edge 470 of the boss 420, the membrane 440 and the relief portion 472 may separate, thereby opening the valve 400. This is depicted in FIG. 4D. When the seal between the top edge 470 and the membrane 440 is thus broken, the liquid (aqueous humor in this example) may flow into the chamber 480. The relief portion 472 provides a bias to the seal between the top edge 470 and the membrane 440, such that a breach in the seal may occur consistently along the relief portion 472, which is opposite the valve outlet 460. By controlling the site of a breach, the liquid 492 may be directed symmetrically to the valve outlet 460 as is depicted in FIGS. 5A, 5B, 5C, and 5D, discussed below.

FIG. 5A is a top view of the valve 400 during a priming process. The priming process may occur prior to implantation beside a patient's eye. Such a process may be performed by a doctor or technician by coupling the valve inlet 450 to a tube, the other end of which is connected to a fluid-filled syringe. As the liquid 492 is injected into the valve 400, it first fills the valve inlet 450 and then fills a volume defined between the top of the boss 420 and the membrane 440. When the pressure exerted by the liquid 492 is greater than a pressure required to separate the relief portion 472 from the membrane 440, an initial breach occurs allowing a volume of the liquid 492 to enter the chamber 480. In FIGS. 5B-5D, the volume of liquid 492 increases as more of the liquid 492 is injected through the valve inlet 450.

In FIG. 5B, the volume increases as more liquid 492 passes through the breach between the membrane 440 and the relief portion 472. As depicted in FIG. 5B, the liquid 492 includes a first front 510A and a second front 510B. The first front 510A and the second front 510B may advance through the chamber 480 at a substantially equal rate. The first front advances through a first portion of the chamber, the first portion being defined from the point of the breach to the outlet 460 in the direction of the movement of the first front 510A. The second front 510B advances through a second portion of the chamber, being defined similarly from the breach to the outlet 460 in the direction of movement of the second front 510B. This may be seen as depicted in FIG. 5C in which the first front 510A and the second front 510B are approaching the valve outlet 460. Then, as seen in FIG. 5D, the first front 510A 512A and the second front 510B may both arrive at the valve outlet 460 at a substantially similar time. In some valves, bubbles may form when one front passes beyond the valve outlet before the other front arrives. By having the first front 510A and the second front 510B moving through the chamber 480 from the breach to the valve outlet 460 over substantially similarly dimensioned paths, the formation of bubbles may be inhibited.

FIG. 6A is a top view of a valve 600 such as may be used in the intraocular device 200 as seen in FIGS. 2 and 3. The valve 600 may be similar in many respects to the valve 400 as described above and depicted in FIGS. 4A-D and 5A-D. Valve 600 includes a substrate 610, a boss 620, a membrane retainer 630, and a flexible membrane 640. In FIG. 6A, the membrane 640 is not clearly shown, while it is more clearly seen in FIG. 6B. The valve 600 may be configured to direct a liquid as it flows from a valve inlet 650, through a chamber 680, and out a valve outlet 660. As depicted in FIG. 6A, the boss 620 may include a circular side (as viewed from above) closest to the valve outlet 660 and a non-circular side (as viewed from above) opposite the valve outlet 660. In some embodiments, the non-circular side opposite the valve outlet 660 may be an elliptical side. The dashed line 622 in FIG. 6A illustrates the deviation of the non-circular side from a circular side. A top edge 670 of the boss 620 includes a relief portion 672 along a top edge of the non-circular side and a non-relief portion 674 along the circular side. Thus, the boss 620 may be symmetric relative to line B-B, and asymmetric relative to a line B'-B' that is orthogonal to line B-B and in plane with the substrate 610.

FIG. 6B is a cross-sectional view of the valve 600 of FIG. 6A along the line B-B. This perspective may provide a clearer depiction of the membrane 640. The chamber 680 may be a toroidal chamber. Due to the geometry of the valve 600, the membrane 640 requires a greater degree of deflection along the non-relief portion 674 than along the relief portion 672 for fluid to pass. Thus, when a sufficiently pressurized fluid enters through the valve inlet 650 and begins exerting outward pressure on the membrane 640, the seal between the membrane and the boss 620 is breached along the relief portion 672. By creating a bias in the seal between the membrane 640 and the boss 620, the flow of liquid from the valve inlet 640 to the valve outlet 660 may be directed through the gap. In this manner, two fronts may be formed as described above and depicted in FIGS. 5A-D.

FIG. 7A is a top view of a valve 700, which is similar in some respects to the valves 400 and 600, described above and depicted in FIGS. 4A-D, 5A-D, and 6A-B. Valve 700 includes a substrate 710, a boss 720, a membrane retainer 730, and a membrane 740. The membrane 740 is present in FIG. 7A, but more clearly depicted in FIG. 7B. The valve 700 may be configured to direct a liquid as it flows from a valve inlet 750, through a chamber 780, and out a valve outlet 760. As depicted in FIG. 7A, the boss 720 may have a generally cylindrical cross-section. The boss 720 is offset from a center of the membrane 740, such that the boss 720 may be closer to the valve outlet 760. The dashed circle 722, depicted in FIG. 7A, illustrates where the boss 720 would be if it were centered relative to the membrane 740. Because of the offsetting, a top edge 770 of the boss 720 may include a relief portion 772 and a non-relief portion 774. The relief portion 772 of the top edge 770 is the side of the top edge 770 that is closer to the center of the membrane 760, while the non-relief portion 774 may be the side of the top edge 770 that is closer to the edges of the membrane 760. Because of the offset toward the outlet 660, the pressure required to separate the membrane 740 from the top edge 770 may be less along the relief portion 772 than along the non-relief portion 774.

FIG. 7B is a cross-sectional view of the valve 700 of FIG. 7A as seen along the line C-C. FIG. 7B may provide additional perspective on the valve 700. For example, a point of the relief portion 772 is depicted along with a point along the non-relief portion 774. When a liquid under sufficient pressure is introduced into the valve inlet 750, the liquid may push against the membrane 740 and the boss 720. This pressure causes a breach to form between the membrane 740 and the top edge 770 of the boss 720 along the relief portion 772. The liquid flow into the chamber 780 at a position opposite the valve outlet 760. Two fronts of the liquid formed that travel to the valve outlet 760 in different directions. Because of the position at which the breach occurs, the two fronts may arrive at the valve outlet 760 at approximately the same time. Thus, neither front may pass beyond the valve outlet 760, which could cause a bubble to form. This may be similar to the movement of the liquid from the valve inlet 450 to the valve outlet 460 as depicted in FIGS. 5A-D.

Figure 8A:
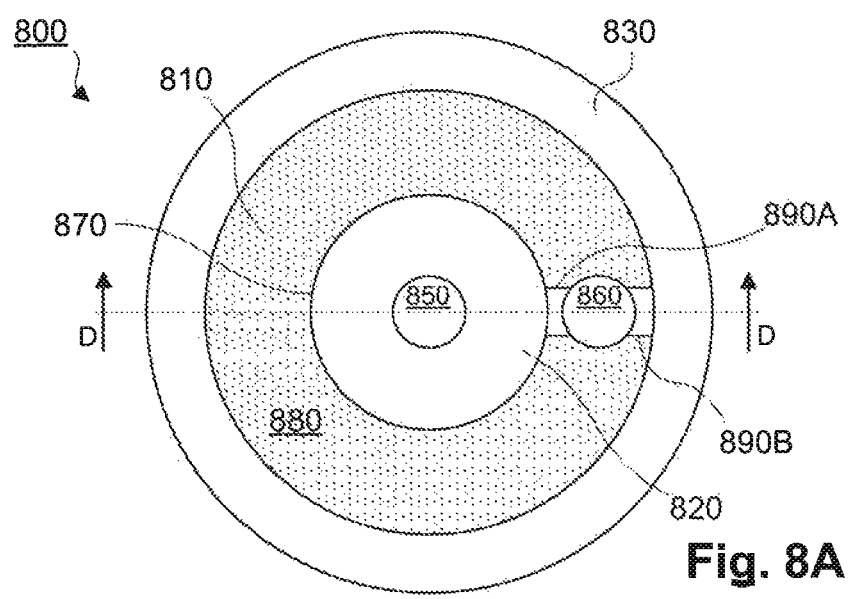
FIG. 8A is a top view of yet another valve such as may be used in the intraocular implant according to exemplary aspects of the present disclosure.

FIG. 8A is a top view of valve 800 such as may be used in an intraocular implant, such as implant 200 discussed above and depicted in FIGS. 2 and 3. The valve 800 may include a substrate 810 with a boss 820 extending up from the substrate 810. In depicted, the boss is generally cylindrical with a circular cross-section. In some embodiments, the boss may have a non-circular cross-section. A membrane retainer 830 may also extend up from the substrate 810 to form a valve portion in combination with the boss 820 by supporting a membrane 840. The membrane retainer 830 has the dome-shaped membrane 840 attached thereto. The membrane 840 contacts the boss 820, applying pressure to a top edge 870 of the boss 820, such that absent sufficient pressure, a liquid may be inhibited from flowing from a valve inlet 850, into a chamber 880, and out through a valve outlet 860. In some embodiments, the substrate 810, the boss 820, and the membrane retainer 830 may be a monolithic structure, while in other embodiments, these components may be fabricated separately from distinct materials, including biocompatible plastics and/or ceramics.

FIG. 8A also depicts two priming blocks, a priming block 890A and a priming block 890B, adjacent to the outlet 860. As depicted, the priming block 890A is situated in between the outlet 860 and the inside wall of chamber 880 as provided by the boss 820. The priming block 890B is positioned in between the outlet 860 and the outside wall of chamber 880 as provided by the membrane retainer 830. In general, when a liquid exerts enough pressure to separate a portion of the membrane 840 from the top edge 870, the liquid enters the chamber 880 and begins flowing clockwise and counterclockwise from the point of entry, with a leading surface of the liquid, or front, moving in each direction toward the outlet 860. The priming block 890A and 890B may inhibit either front from moving into the chamber 880 beyond the outlet 860. The priming blocks 890A and 890B may direct the liquid out through the outlet 860. This may inhibit the formation of gas bubbles within the chamber 880.

Figure 8B:
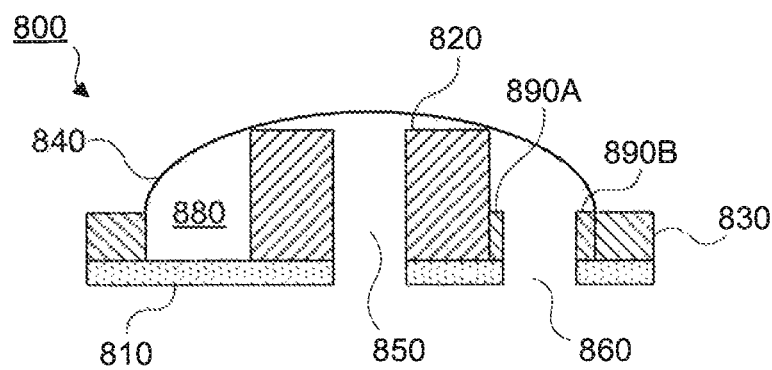
FIG. 8B is a cross-sectional view of the valve of FIG. 8A according to exemplary aspects of the present disclosure.

FIG. 8B is a cross-sectional view of the valve 800 of FIG. 8A along a line D-D. FIG. 8B may provide additional details regarding the valve 800. For example, FIG. 8B depicts the membrane 840 more clearly than FIG. 8A, and also depicts the contact between the membrane 840 and the top edge 870 at two points. When a liquid entering through the inlet 850 exerts sufficient pressure, the seal between the membrane 840 and the top edge 870 is breached, allowing the liquid to enter into the chamber 880. The liquid flows in two directions within the chamber 880, such that the liquid may arrive at the outlet 860 from more than one direction. The priming blocks 890A and 890B may interact with the surface tension of the liquid to inhibit the two flows from meeting within the chamber at a location other than at the outlet 860. By guiding the meeting location of the two flows and the two associated fronts, the priming blocks 890A and 890B may inhibit the formation of gas bubbles within the valve 800.

Figure 9A:
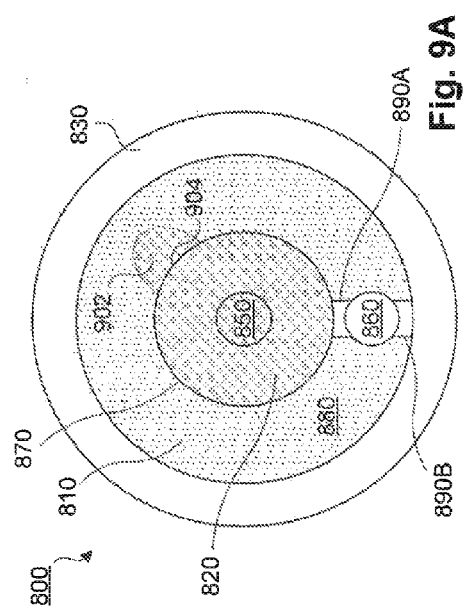
FIGS. 9A, 9B, 9C, and 9D are top views showing the valve of FIGS. 8A and 8B in various stages of priming.

FIGS. 9A, 9B, 9C, and 9D are top views showing the valve 800 of FIGS. 8A and 8B in various stages of priming. As depicted in FIG. 9A, a liquid 902 is introduced through the inlet 850. The pressure exerted by the liquid 902 is sufficient to separate the membrane 840 and the top edge 870 at a location 904, at which the liquid 902 enters the chamber 880. The membrane 840 is transparent in FIGS. 9A, 9B, 9C, and 9D, but more clearly depicted in profile in FIG. 8B.

Figure 9B:
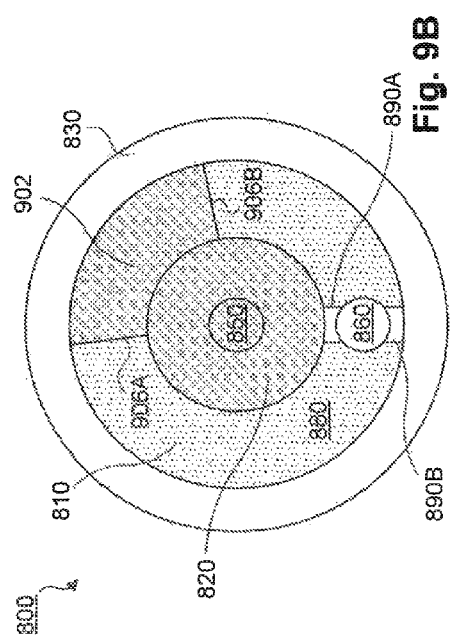

FIG. 9B illustrates a left front 906A that moves through the chamber 880 toward the outlet 860 in a counter-clockwise direction as viewed from above. A right front 906B flows in a clockwise direction from the location 904 to the outlet 860. In general, the left front 906A and the right front 906B may move through the chamber 880 at approximately the same rate. Accordingly, when the location 904 is not exactly opposite the inlet 850 relative to the outlet 860, the left front 906A and the right front 906B may encounter the outlet 860 at different times.

Figure 9C:
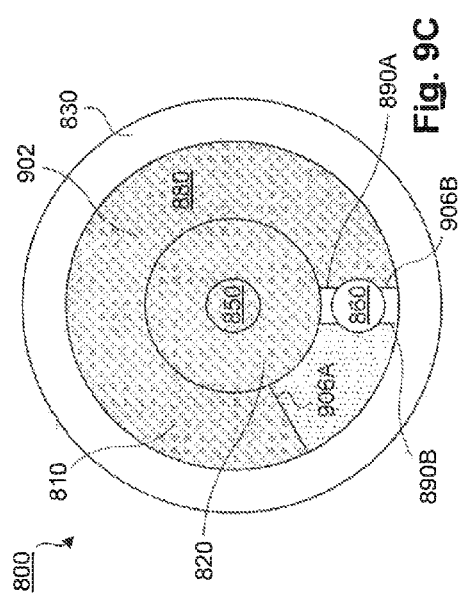
Figure 9D:
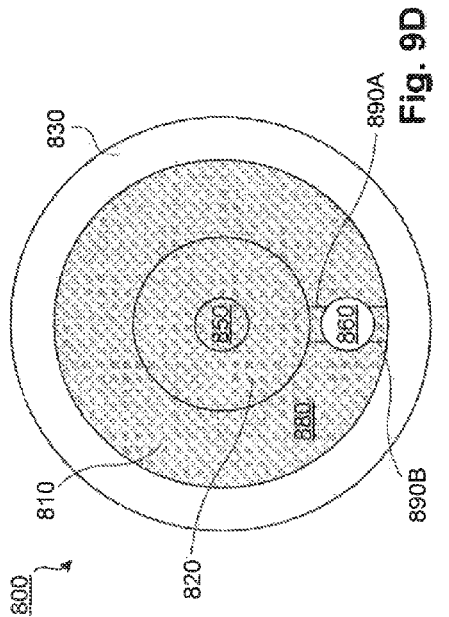

FIG. 9C depicts the right front 906B encountering the priming blocks 890A and 890B, while the left front 906A continues to progress toward the outlet 860. Because the priming blocks inhibit the right front 906B from progressing beyond the outlet 860 toward the left front 906A. As more liquid 902 flows into the chamber 880, the left front 906A progresses toward the outlet 860, at which point the fronts 906A and 906B may meet, allowing liquid from each front to exit through the outlet 860, as depicted in FIG. 9D.

Figure 10:
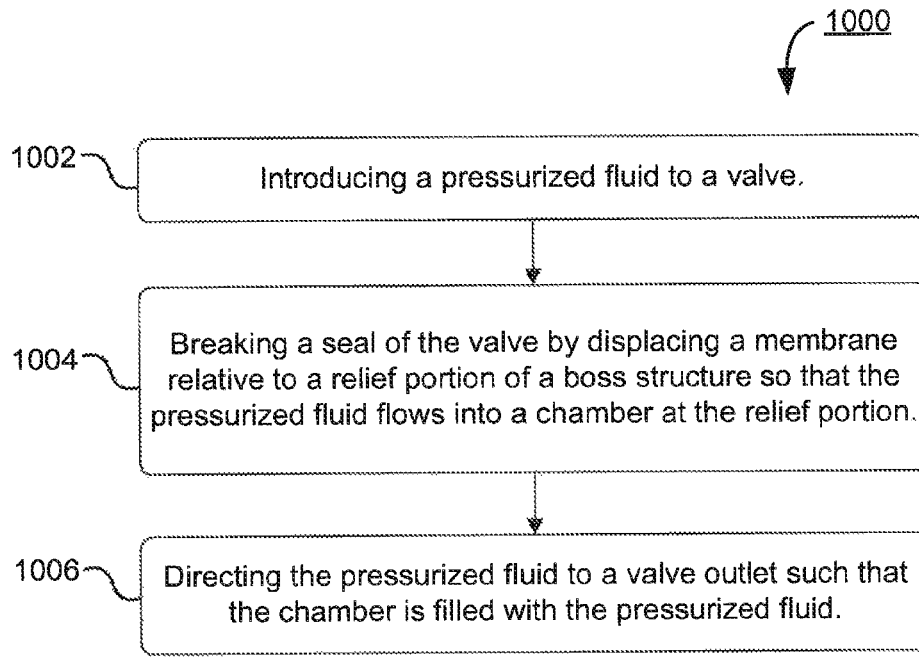
FIG. 10 is a flowchart showing a method of priming a valve in an intraocular device according to exemplary aspects of the present disclosure.

FIG. 10 shows a method 1000 of priming a valve in an intraocular device according to exemplary aspects of the present disclosure. As depicted, the method 1000 includes a number of enumerated steps. However, embodiments of the method 1000 may include additional steps before, in between, and after the enumerated steps. To better describe some embodiments of method 1000, reference will be made to valves 400, 600, and/or 700 as discussed above and depicted in FIGS. 4A-D, 5A-D, 6A-B, and 7A-B. As shown, the method 1000 begins at step 1002, in which a pressurized fluid is introduced to a valve. For example, a doctor or technician may couple a fluid source such as a syringe to the inlet 450 of the valve 400 in an intraocular device 200.

At step 1004, a seal of the valve is broken by displacing a membrane relative to a relief portion of a boss structure. In this way, the pressurized fluid flows into a chamber at the relief portion, while the pressurized fluid is restricted from flowing into the chamber along a non-relief portion. For example, as discussed above, the straightened relief portion 472 may separate from the membrane 440 at a lower fluid pressure than the non-relief portion 474. Thus, as pressure increases in the inlet 450 and in the volume between the top surface of the boss 420 and the membrane 440, the seal at the relief portion 472 breaches while it remains intact along the rest of the top edge 470. In embodiments of the method 1000 that utilize a valve that is similar to the valve 600, the relief portion is provided by a flattened relief portion 672, which has a larger radius of curvature than the non-relief portion 674. In embodiments of the method 1000 that utilize a valve like valve 700, an offset in the position of the boss 720 may decrease the pressure required to break the boss-membrane seal along a relief portion 772 relative to a non-relief portion 774.

At step 1006, the pressurized fluid is directed to the outlet such that the chamber is filled with the pressurized fluid. For example, because the seal between the top edge 470 and the membrane 440 is breached along the relief portion 472, the pressurized fluid enters the chamber 480 opposite the outlet 460 relative to the inlet 450. The liquid may flow in two fronts: one counter-clockwise and the other clockwise. Because the two fronts begin equidistantly from the outlet 460, they may arrive at substantially the same time at the outlet 460. This may drive air or other gas through the outlet 460, which may inhibit the formation of bubbles within the chamber 480. This is shown in FIGS. 5A-D.

Figure 11:
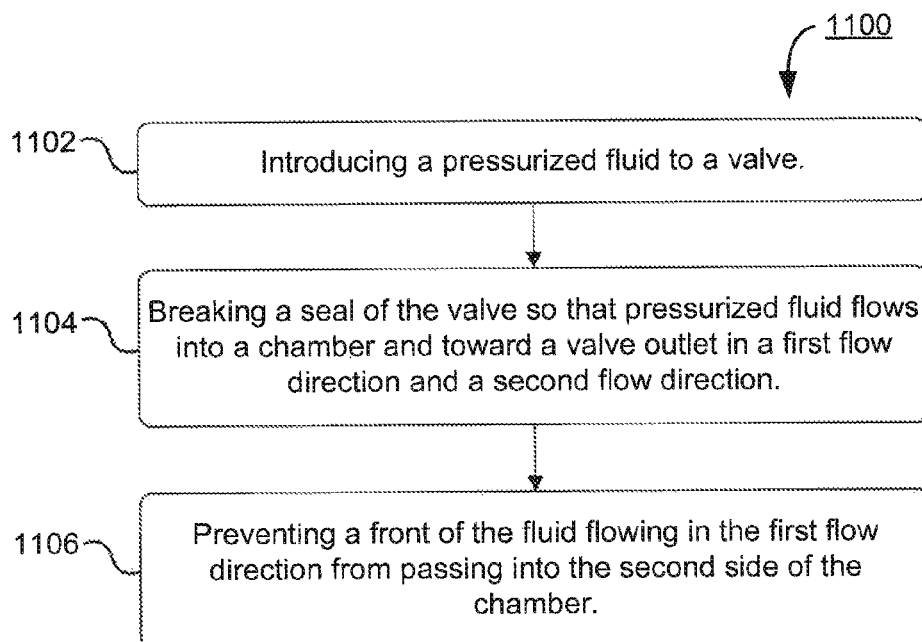
FIG. 11 is a flowchart showing an additional method of priming a valve in an intraocular device according to exemplary aspects of the present disclosure.

FIG. 11 shows a method 1100 of priming a valve in an intraocular device according to exemplary aspects of the present disclosure. As depicted, the method 1100 includes a number of enumerated steps. However, embodiments of the method 1100 may include additional steps before, in between, and after the enumerated steps. To better describe some embodiments of method 1100, reference will be made to valves 400, 600, 700, and/or 800 as discussed above and depicted in FIGS. 4A-D, 5A-D, 6A-B, 7A-B, 8A-B, and/or FIGS. 9A-D. As shown, the method 1100 begins at step 1102, in which a pressurized fluid is introduced to a valve. For example, a doctor or technician may couple a fluid source such as a syringe to the inlet 850 of the valve 800.

At step 1104, the pressurized fluid breaks the seal of the valve so that the fluid flows into a chamber, toward an outlet in both a first flow direction and a second flow direction. As depicted in FIG. 9A, the fluid separates the top edge 870 from the membrane 840 at the location 904, from which liquid 902 flows into the chamber 880. Two fronts form proximate the location 904 with a front 906B flowing in a clockwise direction and a front 906A flowing in a counter-clockwise direction.

At step 1106, a front of the fluid flowing in the first flow direction is prevent or inhibited from passing into a second portion of the chamber, where the second portion of the chamber is associated with the second flow direction and a first portion of the chamber is associated with the first flow direction. As illustrated in FIG. 9C, the front 906B is prevented or inhibited from passing into the second portion of the chamber 880 by priming blocks 890A and 890B. When the front 906B encounters the priming blocks 890A and 890B, the flow of liquid behind front 906B may be directed through the outlet 860, and thereby away from the other side of the chamber. The front 906A may continue progressing toward the outlet 860 in a counter-clockwise direction.

The systems and methods disclosed herein may be used to provide better performance for intraocular devices, such as increased accuracy in pressure measurements. This may be done by guiding two fronts of a liquid and the fronts move through a chamber so as to inhibit the formation of gas bubbles within the chamber. This may result in more effective treatment and more accurate data, thereby improving the overall clinical result.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A microfluidic valve for implantation in an eye of a patient, comprising:
   a chamber formed between a substrate and a flexible membrane;
   a boss disposed in the chamber and having a top edge in selective contact with the flexible membrane, the top edge including a relief portion and a non-relief portion, the relief portion being structurally arranged so that a pressure required to separate the membrane from the relief portion is less than a pressure required to separate the membrane from the non-relief portion, the boss offset from a center of the chamber;
   an inlet extending through the boss and the substrate through which fluid enters the chamber; and
   an outlet configured to allow fluid to exit the chamber, the outlet located opposite the relief portion of the boss such that a fluid entering the inlet displaces the flexible membrane from the boss at the relief portion, travels around the chamber to the outlet thereby substantially filling the chamber, and exits the chamber through the outlet.

2. The microfluidic valve of claim 1, wherein the boss is cylindrical.

3. The microfluidic valve of claim 2, wherein the non-relief portion is circular and the relief portion is circular.

4. The microfluidic valve of claim 2, wherein the boss is an elliptical cylinder.

5. The microfluidic valve of claim 1, wherein the chamber is a toroidal chamber.

6. The microfluidic valve of claim 1, wherein the inlet is smaller in diameter than the outlet.

7. The microfluidic valve of claim 1, wherein the relief portion and the outlet port are on opposite sides of the inlet port.

8. The microfluidic valve of claim 1, wherein the outlet is formed through the substrate.

9. The microfluidic valve of claim 1 wherein the chamber comprises a first wall and a second wall, the second wall opposing the first wall.

10. The microfluidic valve of claim 9 further comprising a first priming block disposed between the outlet and the first wall and by a second priming block disposed between the outlet and the second wall.

11. The microfluidic valve of claim 10 wherein the first wall is formed by the boss.

12. The microfluidic valve of claim 10, wherein the first and second priming blocks are configured to inhibit the flow of a liquid from one side of the first and second priming blocks to another side within the chamber.

13. A microfluidic valve for implantation in an eye of a patient, comprising:
   a chamber formed between a substrate and a flexible membrane, the chamber having a boundary surface comprising a first wall and a second wall, the second wall opposing the first wall;
   a boss disposed in the chamber and having a top edge in selective contact with the flexible membrane, the top edge including a relief portion and a non-relief portion, the relief portion being structurally arranged so that a pressure required to separate the membrane from the relief portion is less than a pressure required to separate the membrane from the non-relief portion, the boss offset from a center of the chamber;
   an inlet extending through the boss and the substrate through which fluid enters the chamber; and
   an outlet configured to allow the fluid to flow out of the chamber through a location accessible to fluid flowing to the outlet from more than one direction, the outlet being bounded by a first priming block disposed between the outlet and the first wall and by a second priming block disposed between the outlet and the second wall, the outlet located opposite the relief portion of the boss such that a fluid entering the inlet displaces the flexible membrane from the boss at the relief portion, travels around the chamber to the outlet thereby substantially filling the chamber, and exits the chamber through the outlet.

* * * * *